United States Patent
Duan et al.

(10) Patent No.: US 12,419,312 B2
(45) Date of Patent: Sep. 23, 2025

(54) ***BACILLUS VELEZENSIS* STRAIN FOR PREVENTING AND CONTROLLING EARLY BOLTING OF *ANGELICA SINENSIS*, MICROBIAL AGENT AND USE THEREOF**

(71) Applicant: NANJING UNIVERSITY OF CHINESE MEDICINE, Nanjing (CN)

(72) Inventors: Jinao Duan, Nanjing (CN); Pei Liu, Nanjing (CN); Hui Yan, Nanjing (CN); Weimeng Feng, Nanjing (CN); Sheng Guo, Nanjing (CN); Sen Zhang, Nanjing (CN)

(73) Assignee: NANJING UNIVERSITY OF CHINESE MEDICINE, Nanjing (CN)

( * ) Notice: Subject to any disclaimer, the term of this patent is extended or adjusted under 35 U.S.C. 154(b) by 0 days.

(21) Appl. No.: 18/754,225

(22) Filed: Jun. 26, 2024

(65) Prior Publication Data
US 2024/0341311 A1 Oct. 17, 2024

(30) Foreign Application Priority Data
Dec. 28, 2023 (CN) .......................... 202311832429.2

(51) Int. Cl.
*A01N 63/22* (2020.01)
*A01P 21/00* (2006.01)
*C12N 1/20* (2006.01)
*C12R 1/07* (2006.01)

(52) U.S. Cl.
CPC .............. *A01N 63/22* (2020.01); *A01P 21/00* (2021.08); *C12N 1/205* (2021.05); *C12R 2001/07* (2021.05)

(58) Field of Classification Search
CPC ......... A01N 63/22; A01P 21/00; C12N 1/205; C12N 1/20; C12N 1/02; C12R 2001/07; A01C 1/00; A01G 7/06
See application file for complete search history.

(56) References Cited

FOREIGN PATENT DOCUMENTS

WO 2017081105 A1 5/2017

OTHER PUBLICATIONS

Rabbee, M.F. et al., Bacillus velezensis: A Valuable Member of Bioactive Molecules within Plant Microbiomes, 2019, Molecules, vol. 24, Issue 1046, pp. 1-13. (Year: 2019).*
Rabbee, M.F. et al., Bacillus velezensis: A Beneficial Biocontrol Agent or Facultative Phytopathogen for Sustainable Agriculture, 2023, Agronomy, vol. 13, Issue 840, pp. 1-14. (Year: 2023).*
Liu, P. et al., CN114045242A, Bacillus velezensis XG2 strain for producing phthalide components and application of bacillus velezensis XG2 strain, 2022, Espacenet English Translation, 6 pages. (Year: 2022).*
Haichao Feng et,Listening to plant's Esperanto via root exudates: reprogramming the functional expression of plant growth-promoting rhizobacteria New Phytologist: p. 2307-2319 Publication Date: Jun. 25, 2023.

* cited by examiner

*Primary Examiner* — Ali Soroush
*Assistant Examiner* — Andriae M Holt
(74) *Attorney, Agent, or Firm* — CBM PATENT CONSULTING, LLC

(57) ABSTRACT

A strain separation method for preventing and controlling early bolting of *Angelica sinensis*, and preparation of a microbial agent and use thereof, the strain is obtained by separation, purification and cultivation from rhizosphere soil of *Angelica sinensis*, and is identified as *Bacillus* spp. by Microbial 16S rDNA sequencing; the strain was deposited at China Center for Type Culture Collection on Jun. 24, 2021 under CCTCC NO: M 2021767; tThe *Bacillus velezensis* XG3 strain provided by the present invention can promote the seed germination of *Angelica sinensis* and delay the flowering of *Arabidopsis thaliana* for about 2 days; according to field test verification, the microbial agent can increase the root weight, root diameter and rootlet number of *Angelica sinensis*, can effectively prevent and control early bolting of *Angelica sinensis*.

1 Claim, 7 Drawing Sheets
Specification includes a Sequence Listing.

```
                        SEQUENCE LISTING

Sequence total quantity: 3
SEQ ID NO: 1            moltype = DNA  length = 18
FEATURE                 Location/Qualifiers
source                  1..18
                        mol_type = other DNA
                        organism = synthetic construct
SEQUENCE: 1
agtttgatcm tggctcag                                                18

SEQ ID NO: 2            moltype = DNA  length = 19
FEATURE                 Location/Qualifiers
source                  1..19
                        mol_type = other DNA
                        organism = synthetic construct
SEQUENCE: 2
ggttaccttg ttacgactt                                               19

SEQ ID NO: 3            moltype = DNA  length = 1486
FEATURE                 Location/Qualifiers
source                  1..1486
                        mol_type = genomic DNA
                        organism = Bacillus velezensis
SEQUENCE: 3
ggctcaggac gaacgctggc ggcgtgccta atacatgcaa gtcgagcgga cagatgggag    60
cttgctccct gatgttagcg gcggacgggt gagtaacacg tgggtaacct gcctgtaaga   120
ctgggataac tccgggaaac cggggctaat accggatggt tgtttgaacc gcatggttca   180
gacataaaag gtggcttcgg ctaccactta cagatgaccc cgcggcgcat tagctagttg   240
gtgaggtaac ggctcaccaa ggcaacgatg cgtagccgac ctgagagggt gatcggccac   300
actgggactg agacacggcc cagactccta cgggaggcag cagtagggaa tcttccgcaa   360
tggacgaaag tctgacggag caacgccgcg tgagtgatga aggttttcgg atcgtaaagc   420
tctgttgtta gggaagaaca agtgccgttc aaatagggcg gcaccttgac ggtacctaac   480
cagaaagcca cggctaacta cgtgccagca gccgcggtaa tacgtaggtg gcaagcgttg   540
tccggaatta ttgggcgtaa agggctcgca ggcggttttc ttaagtctgat gtgaaagccc   600
ccggctcaac cggggagggt cattggaaac tggggaactt gagtgcagaa gaggagagtg   660
gaattccacg tgtagcggtg aaatgcgtag agatgtggag gaacaccagt ggcgaaggcg   720
actctctggt ctgtaactga cgctgaggag cgaaagcgtg gggagcgaac aggattagat   780
accctggtag tccacgccgt aaacgatgag tgctaagtgt taggggtttt ccgcccctta   840
gtgctgcagc taacgcatta agcactccgc ctggggagta cggtcgcaag actgaaactc   900
aaaggaattg acggggccc gcacaagcgg tggagcatgt ggtttaattc gaagcaacgc   960
gaagaacctt accaggtctt gacatcctct gacaatccta gagataggac gtcccttcg   1020
ggggcagagt gacaggtggt gcatggttgt cgtcagctcg tgtcgtgaga tgttgggtta   1080
agtcccgcaa cgagcgcaac ccttgatctt agttgccagc attcagttgg gcactctaag   1140
gtgactgccg gtgacaaacc ggaggaaggt ggggatgacg tcaaatcatc atgccccta   1200
tgacctgggc tacacacgtg ctacaatgga cagaacaaag ggcagcgaaa ccgcgaggtt   1260
aagccaatcc cacaaatctg ttctcagttc ggatcgcagt ctgcaactcg actgcgtgaa   1320
gctggaatcg ctagtaatcg cggatcagca tgccgcggtg aatacgttcc cgggccttgt   1380
acacaccgcc cgtcacacca cgagagtttg taacacccga agtcggtgag gtaacctttt   1440
aggagccagc cgccgaaggt gggacagatg attggggtga agtcgt               1486
```

BACILLUS VELEZENSIS STRAIN FOR PREVENTING AND CONTROLLING EARLY BOLTING OF ANGELICA SINENSIS, MICROBIAL AGENT AND USE THEREOF

REFERENCE TO AN ELECTRONIC SEQUENCE LISTING

The contents of the electronic sequence listing (240662.xml; Size: 5,275 bytes; and Date of Creation: Jun. 12, 2024) is herein incorporated by reference in its entirety.

CROSS-REFERENCE TO RELATED APPLICATIONS

This application claims priority to Chinese Patent Application Ser. No. CN2023118324292 filed on 28 Dec. 2023.

TECHNICAL FIELD

The present invention relates to a *Bacillus velezensis* strain, in particular, relates to a strain capable of promoting seed germination and plant growth of *Angelica sinensis*. A microbial agent prepared from the strain can be used for preventing and controlling early bolting of *Angelica sinensis* and increasing the yield of *Angelica sinensis*, and belongs to the technical field of microorganisms.

BACKGROUND

*Angelica sinensis* is used as a low-temperature long-day perennial plant, and the whole growth and development period is generally 3 years. In the first year, seedlings are sown in mountainous regions from June to July, and harvested from October to November for cellar storage. In the second year, seedlings are transplanted and planted before and after the Qingming festival, the adult *Angelica sinensis* starts to be dug from late October to early November, and some seedlings are reserved until the third year for bolting, flowering and seed bearing for subsequent planting. However, in the actual production process, the growth of *Angelica sinensis* is easily affected by various ecological factors. In the second year, *Angelica sinensis* is early bolting and flowering in the vegetative growth stage, the fleshy roots are aging, fats and oils are reduced, the content of pharmacodynamic active ingredients is reduced, the quality of the medicinal materials is reduced, and the yield and the daily supply of *Angelica sinensis* are seriously influenced. The situation of early bolting of *Angelica sinensis* was investigated nationwide in 1980s. The results showed that the early bolting rate in Min County of Gansu Province was 10%-30% in normal years, and it was as high as 80% in severe cases; the early bolting rate in Baoji City of Shaanxi Province was about 30%, and it was as high as 90% in severe cases. In 2020, the situation of early bolting of *Angelica sinensis* in 10 townships in Dingxi, Longnan, Zhangye and Gannan Tibetan Autonomous Prefecture of Gansu Province was investigated. The results showed that the early bolting rate in 30 planting areas ranged from 11% to 86%, with an average of 51.62%. After nearly 40 years' development, the problem of early bolting of *Angelica sinensis* still exists or even becomes more and more serious. How to better decrease the early bolting rate in the production process of *Angelica sinensis* has become a bottleneck problem restricting the sustainable development of the *Angelica sinensis* industry.

Although a lot of research has been carried out on the problem of early bolting of *Angelica sinensis*, the situation of early bolting of *Angelica sinensis* is still very serious, which can be avoided by controlling seedlings and strengthening field management, etc., but the situation is still not optimistic. The formation mechanism of early bolting of *Angelica sinensis* is complex, including internal factors such as seeds and seedlings, and external factors such as storage, fertilization, transplanting density and soil. Although big seedlings that are easy to bolt can be removed during seedling selection, the early bolting of *Angelica sinensis* can only be found after the seedlings are subjected to bolting, and at this time, it is too late to replenish seedlings. The average bolting rate of about 30% is seriously harmful to the yield of *Angelica sinensis* and the economic benefits of peasants, some peasants choose to increase the planting quantity to make up for it in order to reduce the impact of early bolting on the yield and benefits, but the high planting density easily causes the early bolting of *Angelica sinensis*. How to discover the problem earlier so as to intervene earlier and reduce the adverse effect on the *Angelica sinensis* medicinal material industry becomes a problem worthy of consideration. In recent years, with the deepening of the research on microbial fertilizers, microbial agents have been widely recognized for their green, efficient and safe characteristics, so the abundant microbial resources of *Angelica sinensis* are further developed and applied to the prevention and control of early bolting of *Angelica sinensis*, or the microbial agents are applied to the planting process instead of the traditional fertilizers and pesticides, such that the accumulation of pesticide residues in *Angelica sinensis* is reduced, and the high-quality, high-yield and green planting of *Angelica sinensis* can be better served.

SUMMARY

Objective: the present invention aims to provide a *Bacillus velezensis* XG3 strain for preventing and controlling early bolting of *Angelica sinensis*, a method for separating, fermenting and culturing the strain and a preparation method for a microbial agent. Another objective of the present invention is to provide use of the strain in the processes of seed germination and plant growth of *Angelica sinensis*, and use of a microbial agent of the strain in preventing and controlling early bolting in the process of production and cultivation of *Angelica sinensis*.

Technical solutions: in order to achieve the above objectives, the present invention adopts the following technical solutions:

The *Bacillus velezensis* XG3 strain for preventing and controlling early bolting of *Angelica sinensis* provided by the present invention is obtained by separation, purification and cultivation from rhizosphere soil of *Angelica sinensis*, and is identified as *Bacillus* spp. by Microbial 16S rDNA sequencing. The strain was deposited at China Center for Type Culture Collection on Jun. 24, 2021 under CCTCC NO: M 2021767, and classified and named as *Bacillus velezensis* XG3; the 16S rDNA sequence of the strain is shown in Sequence listing.

The method for separating, fermenting and culturing the *Bacillus velezensis* XG3 strain provided by the present invention comprises oscillation, inoculation, separation, cultivation and preservation, and specifically comprises the following steps:

a) oscillation: stripping soil around the root of *Angelica sinensis*, shaking off, collecting rhizosphere surface soil, placing 5 g of the soil in a triangular flask containing 100 mL of sterile water, oscillating the flask on a thermostatic shaker at 37° C. for 2 h at 160 r/min, standing for 30 min to obtain a soil stock solution ($10^{-1}$), pipetting 1 mL of a supernatant by using a pipettor, adding the supernatant into 9 mL of sterile water, fully shaking and uniformly mixing the mixture to obtain a soil diluent ($10^{-2}$), and repeating the steps to obtain soil diluents ($10^{-1}$-$10^{-6}$);

b) separation: pipetting 0.1 mL of the soil diluents ($10^{-4}$, $10^{-5}$ and $10^{-6}$), and inoculating the soil diluents into a prepared LB solid culture medium, with 3 replicates per dilution; inverting the plate, culturing the plate at 37° C., observing growth conditions of colonies at any time, inoculating bacteria with different forms in an LB solid culture medium by using an inoculating loop, and repeatedly purifying until a single colony is obtained; and c) cultivation and preservation: picking the bacteria purified on the plate into a triangular flask containing an LB liquid culture medium, oscillating the flask on a thermostatic shaker at 37° C. for 24 h at 160 r/min, mixing the bacteria with 50% glycerol at a volume ratio of 1:1, then placing the mixture into a sterilized cryopreservation tube, uniformly mixing the mixture, sealing the tube by a sealing film, and storing the tube in an ultra-low temperature refrigerator at −80° C.

Provided is a preparation method for a microbial agent for preventing and controlling early bolting of *Angelica sinensis*, which comprises the following steps: inoculating the *Bacillus velezensis* XG3 strain into an LB liquid culture medium, performing activation culture on a thermostatic shaker, then transferring the activated strain to a triangular flask containing an LB liquid culture medium for fermentation, culturing the strain on a shaker, centrifuging a fermentation liquor, collecting a bacterial precipitate, adding a composite protectant prepared from sucrose, trehalose, sodium glutamate and glucose, and lyophilizing in vacuum to obtain a lyophilized powder of the microbial agent.

As a preferred embodiment, the preparation method for a microbial agent of the *Bacillus velezensis* XG3 strain provided by the present invention comprises the following steps: inoculating the *Bacillus velezensis* XG3 strain in an LB liquid culture medium, performing activation culture on a thermostatic shaker at 37° C. for 24 h at 140 r/min, then transferring the strain activated overnight at a ratio of 1% (v/v) to a new LB liquid culture medium, culturing the strain at 140 r/min for 24 h, measuring an OD value thereof, centrifuging a fermentation liquor at 4000 rpm for 5 min, then discarding the supernatant, and collecting a bacterial precipitate; and dissolving the bacterial precipitate in a composite protectant solution to obtain a bacterial solution (the composite protectant solution is composed of 15 mg/mL glucose, 5.37 mg/mL sucrose, 1.26 mg/mL trehalose and 1.87 mg/mL sodium glutamate), then pre-freezing the sample into an ultra-low temperature refrigerator at −80° C., after the pre-freezing is completed, quickly transferring the sample into a vacuum lyophilizer, lyophilizing at −40° C. and 10 Pa, finally grinding the lyophilized substance, namely lyophilizing in vacuum, to obtain a lyophilized powder microbial agent.

The *Bacillus velezensis* XG3 strain obtained by separation can be used for promoting seed germination and plant growth of *Angelica sinensis*, the fermentation liquor is obtained according to the above fermentation method, and then diluted into bacterial solutions with different OD concentrations, and the bacterial solutions were co-cultured with the *Angelica sinensis* seeds and *Arabidopsis thaliana*.

Provided is use of the microbial agent of the *Bacillus velezensis* XG3 strain prepared by the present invention in preventing and controlling early bolting in the process of production and cultivation of *Angelica sinensis*. The microbial agent obtained by the above preparation method is dissolved in water into solutions with different dosages, and the solutions are co-cultured with *Angelica sinensis*.

Beneficial effects: compared with the prior art, the present invention has the following advantages:

The *Bacillus velezensis* XG3 strain provided by the present invention can promote seed germination of *Angelica sinensis* and delay flowering time of *Arabidopsis thaliana*, and the prepared microbial agent can increase the yield of *Angelica sinensis* and prevent and control early bolting of *Angelica sinensis*, can be subsequently used for developing a multi-effect composite microbial fertilizer which is low in cost, pollution-free, stable in yield increase and capable of effectively preventing and controlling early bolting of *Angelica sinensis*, is further applied to the green and healthy planting industry of *Angelica sinensis*, and is beneficial to green and sustainable development of the *Angelica sinensis* industry.

DETAILED DESCRIPTION

Figure 1:
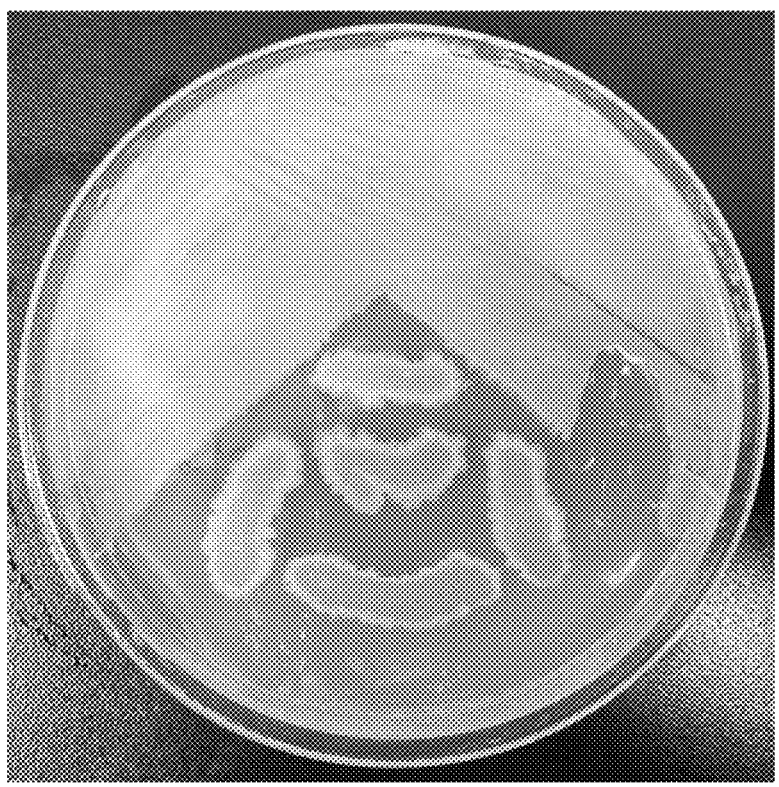
FIG. 1 is a front view of a colony of *Bacillus velezensis* XG3 strain.
Figure 2:
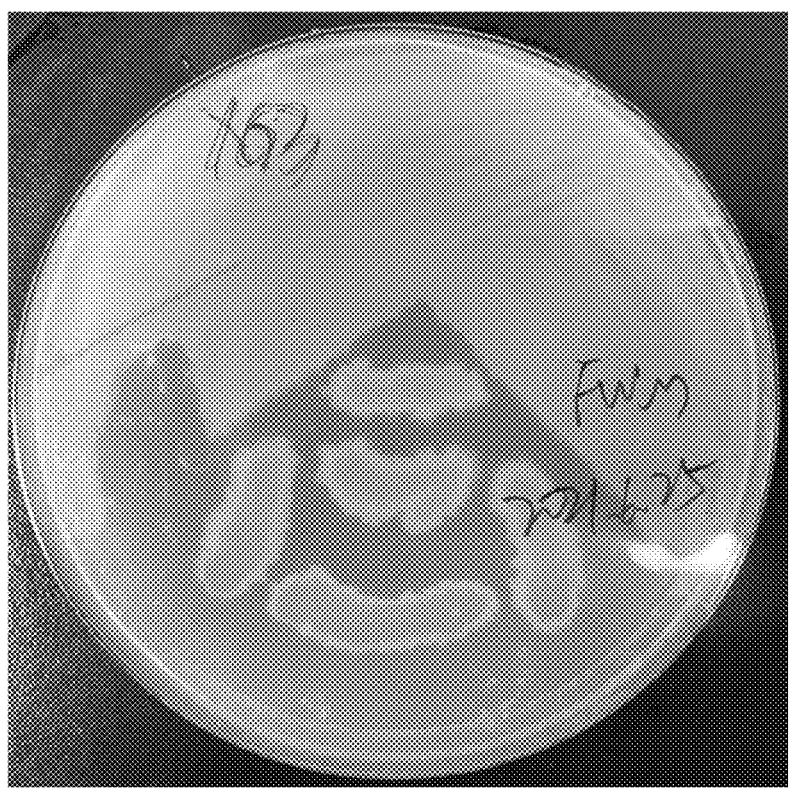
FIG. 2 is a back view of a colony of *Bacillus velezensis* XG3 strain.

The present invention can be better understood according to the following examples. However, it is easily understood by those skilled in the art that the specific fermentation culture process and functional evaluation described in the examples are only used to illustrate the present invention, and should not and will not limit the present invention described in detail in the claims.

The chemical reagents used in the following examples are all commercially available from conventional sources.

Example 1

A new *Bacillus velezensis* XG3 strain was obtained by separation according to the following method:

(1) oscillation: stripping soil around the root of *Angelica sinensis*, shaking off and collecting rhizosphere surface soil, placing 5 g of the soil in a triangular flask containing 100 mL of sterile water, oscillating the flask on a thermostatic shaker at 37° C. for 2 h at 140 r/min, standing for 30 min to obtain a soil stock solution ($10^{-1}$), pipetting 1 mL of a supernatant by using a pipettor, adding the supernatant into 9 mL of sterile water, fully shaking and uniformly mixing the mixture to obtain a soil diluent ($10^{-2}$), and repeating the steps to obtain soil diluents ($10^{-1}$-$10^{-6}$);
(2) separation: pipetting 0.1 mL of the soil diluents ($10^{-4}$, $10^{-5}$ and $10^{-6}$), and inoculating the soil diluents into a prepared LB solid culture medium (composed of 10 g/L peptone, 5 g/L yeast extract, and 10 g/L NaCl), with 3 replicates per dilution; inverting the plate, culturing the plate at 30° C., observing growth conditions of colonies at any time, inoculating bacteria with different forms in an LB solid culture medium by using an inoculating loop, and repeatedly purifying until a single colony is obtained; and
(3) cultivation and preservation: picking the bacteria purified on the plate into a triangular flask containing an LB liquid culture medium, oscillating the flask on a thermostatic shaker at 37° C. for 24 h at 140 r/min, mixing the bacteria with 50% glycerol at a ratio of 1:1, then placing the mixture into a sterilized cryopreservation tube, uniformly mixing the mixture, sealing the tube by a sealing film, and storing the tube in an ultra-low temperature refrigerator at −80° C.

Example 2

The new *Bacillus velezensis* XG3 strain obtained by separation was subjected to molecular identification by the following method:

The *Bacillus velezensis* XG3 strain was fermented and cultured according to the method of Example 1, and the bacterial solution was sent to Sangon Biotech (Shanghai) Co., Ltd. for 16r DNA sequencing. The upstream primer was 27F (5'-AGTTTGATCMTGGCTCAG-3' (SEQ ID NO: 1)), the downstream primer was 1492R (5'-GGTTACCTTGT-TACGACTT-3' (SEQ ID NO: 2)), and the 16Sr DNA sequences were aligned based on ribosomal database and analyzed through Blast sequence alignment analysis. As shown in Table 1, the XG3 strain had 100.0% homology to *Bacillus velezensis*, which was identified as *Bacillus*, and presumed to be *Bacillus velezensis*.

The sequence of the strain was as follows:

```
                                        (SEQ ID NO: 3)
GGCTCAGGACGAACGCTGGCGGCGTGCCTAATACATGCAAGTCGAGCGG

ACAGATGGGAGCTTGCTCCCTGATGTTAGCGGCGGACGGGTGAGTAACA

CGTGGGTAACCTGCCTGTAAGACTGGGATAACTCCGGGAAACCGGGGCT

AATACCGGATGGTTGTTTGAACCGCATGGTTCAGACATAAAAGGTGGCT

TCGGCTACCACTTACAGATGGACCCGCGGCGCATTAGCTAGTTGGTGAG

GTAACGGCTCACCAAGGCAACGATGCGTAGCCGACCTGAGAGGGTGATC

GGCCACACTGGGACTGAGACACGGCCCAGACTCCTACGGGAGGCAGCAG

TAGGGAATCTTCCGCAATGGACGAAAGTCTGACGGAGCAACGCCGCGTG

AGTGATGAAGGTTTTCGGATCGTAAAGCTCTGTTGTTAGGGAAGAACAA

GTGCCGTTCAAATAGGGCGGCACCTTGACGGTACCTAACCAGAAAGCCA

CGGCTAACTACGTGCCAGCAGCCGCGGTAATACGTAGGTGGCAAGCGTT

GTCCGGAATTATTGGGCGTAAAGGGCTCGCAGGCGGTTTCTTAAGTCTG

ATGTGAAAGCCCCCGGCTCAACCGGGGAGGGTCATTGGAAACTGGGGAA

CTTGAGTGCAGAAGAGGAGAGTGGAATTCCACGTGTAGCGGTGAAATGC

GTAGAGATGTGGAGGAACACCAGTGGCGAAGGCGACTCTCTGGTCTGTA

ACTGACGCTGAGGAGCGAAAGCGTGGGGAGCGAACAGGATTAGATACCC

TGGTAGTCCACGCCGTAAACGATGAGTGCTAAGTGTTAGGGGGTTTCCG

CCCCTTAGTGCTGCAGCTAACGCATTAAGCACTCCGCCTGGGGAGTACG

GTCGCAAGACTGAAACTCAAAGGAATTGACGGGGCCCGCACAAGCGGT

GGAGCATGTGGTTTAATTCGAAGCAACGCGAAGAACCTTACCAGGTCTT

GACATCCTCTGACAATCCTAGAGATAGGACGTCCCCTTCGGGGGCAGAG

TGACAGGTGGTGCATGGTTGTCGTCAGCTCGTGTCGTGAGATGTTGGGT

TAAGTCCCGCAACGAGCGCAACCCTTGATCTTAGTTGCCAGCATTCAGT

TGGGCACTCTAAGGTGACTGCCGGTGACAAACCGGAGGAAGGTGGGGAT

GACGTCAAATCATCATGCCCCTTATGACCTGGGCTACACACGTGCTACA

ATGGACAGAACAAAGGGCAGCGAAACCGCGAGGTTAAGCCAATCCCACA

AATCTGTTCTCAGTTCGGATCGCAGTCTGCAACTCGACTGCGTGAAGCT

GGAATCGCTAGTAATCGCGGATCAGCATGCCGCGGTGAATACGTTCCCG

GGCCTTGTACACACCGCCCGTCACACCACGAGAGTTTGTAACACCCGAA

GTCGGTGAGGTAACCTTTTAGGAGCCAGCCGCCGAAGGTGGGACAGATG

ATTGGGGTGAAGTCGT.
```

TABLE 1

XG3 strain sequence alignment results

| Description | Max Score | Total Score | Query Cover | E value | Per. Ident | Accession |
|---|---|---|---|---|---|---|
| *Bacillus velezensis* strain KKLW chromosome, complete genome | 2745 | 24640 | 100% | 0.0 | 100.00% | CP054714.1 |
| *Bacillus velezensis* strain B268 chromosome, complete genome | 2745 | 24557 | 100% | 0.0 | 100.00% | CP053764.1 |
| *Bacillus velezensis* strain S4 chromosome, complete genome | 2745 | 24629 | 100% | 0.0 | 100.00% | CP050424.1 |
| *Bacillus velezensis* strain UB2017 chromosome, complete genome | 2745 | 24651 | 100% | 0.0 | 100.00% | CP049741.1 |
| *Bacillus velezensis* strain SRCM102752 chromosome, complete genome | 2745 | 24553 | 100% | 0.0 | 100.00% | CP028961.1 |

TABLE 1-continued

XG3 strain sequence alignment results

| Description | Max Score | Total Score | Query Cover | E value | Per. Ident | Accession |
|---|---|---|---|---|---|---|
| *Bacillus amyloliquefaciens* strain DGL1 chromosome, complete genome | 2745 | 24646 | 100% | 0.0 | 100.00% | CP065539.1 |
| *Bacillus velezensis* strain KMU01 chromosome, complete genome | 2745 | 24590 | 100% | 0.0 | 100.00% | CP063768.1 |
| *Bacillus velezensis* strain BSC16a chromosome, complete genome | 2745 | 24618 | 100% | 0.0 | 100.00% | CP062074.1 |
| *Bacillus amyloliquefaciens* strain MOH1-5b chromosome, complete genome | 2745 | 24607 | 100% | 0.0 | 100.00% | CP061853.1 |
| *Bacillus velezensis* strain BIOMA BV10 chromosome, complete genome | 2745 | 24540 | 100% | 0.0 | 100.00% | CP059318.1 |

Example 3

The effect of the *Bacillus velezensis* XG3 strain on seed germination of *Angelica sinensis* was tested by the following method:

600 *Angelica sinensis* seeds with full seeds and uniform quality were preferably selected, every 150 seeds were put into 1 culture flask, the flasks numbered 1-4 were separately sterilized with 75% ethanol for 1 min, sterilized with mercury dichloride for 9 min, and rinsed with sterile water for 5 times, and the sterile water was poured out. The *Bacillus velezensis* XG3 bacterial solution obtained according to the fermentation culture method of Example 2 was diluted and measured for OD600 values, and 50 mL of the diluted XG3 bacterial solutions (OD600 values were 0.05, 0.5 and 1, respectively) were poured into the No. 1-3 flasks, respectively, and 50 mL of an LB liquid culture medium was poured into the No. 4 flask and immersed for 24 h. Then, the seeds were transferred to culture dishes with 2 layers of sterile filter paper, 30 seeds were placed in order in each culture dish, and 5 replicates were set for each sample; about 5 mL of sterile water was poured to fully saturate the seeds and the filter paper, and the culture dish was sealed by a sealing film to prevent pollution. The culture dish and the seeds were weighed together and recorded. Then the culture dish was placed in an illumination incubator for incubation, the culture dish was weighed every 24 h, the weight of the culture dish was made up to the original weight, and the germination number of the seeds was recorded. The contaminated seeds were removed in time by using sterile tweezers. The results are shown in Table 2, and the *Bacillus velezensis* XG3 bacterial solutions obtained by screening can promote seed germination of *Angelica sinensis*.

Example 4

Figure 3:
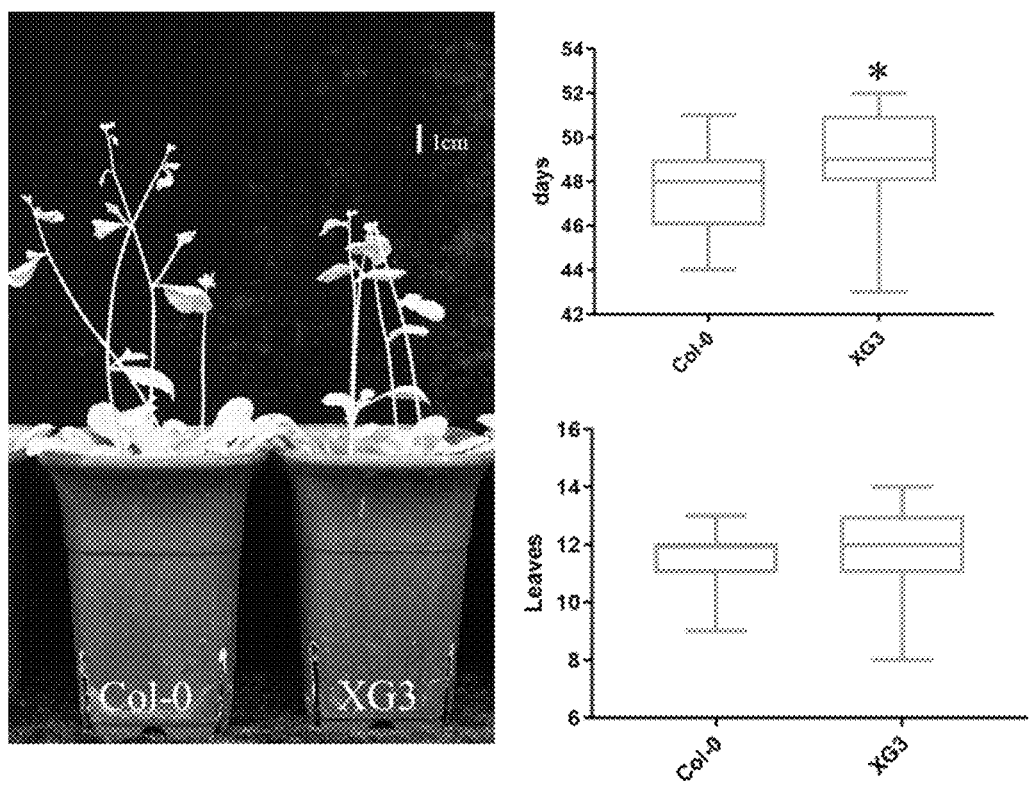
FIG. 3 shows the effect of *Bacillus velezensis* XG3 on flowering of *Arabidopsis thaliana*.

The effect of *Bacillus velezensis* XG3 on flowering of *Arabidopsis thaliana* was investigated by the following method:

A proper amount of Col-0 *Arabidopsis thaliana* seeds were taken and sterilized with 75% ethanol (v/v) for 5 min, sterilized with 5% sodium hypochlorite for 5 min, and then repeatedly washed with sterile water for 4-6 times, 1 min each time; the sterilized seeds were then placed into a ½ MS culture medium, with 15-20 seeds per flask, to ensure uniform distribution among seeds and proper density for later growth and transplantation. When the *Arabidopsis thaliana* seedlings grew to 4-6 leaves, about 2-3 weeks after formal culture, the *Arabidopsis thaliana* seedlings with relatively consistent growth states were slowly taken out from the culture medium by using tweezers, the culture medium on the roots was removed, and the seedlings were transplanted into prepared matrix soil. The matrix soil was prepared by uniformly mixing peat soil, vermiculite and perlite at a ratio of 1:1:1, and sterilized at 121° C. for 15 min. After the seedlings were transferred into the matrix soil for adaptive culture for 3 days, the XG3 liquid strain was inoculated by adopting a root irrigation method, the seedlings were irrigated and inoculated once a week until they fully bloomed, and the growth state, the flowering time and the number of flowering rosette leaves of *Arabidopsis thaliana* were observed and recorded. The results are shown in FIG. 3: blank water was given to the control group, and there was a remarkable late flowering phenomenon when the *Arabidopsis thaliana* was treated with XG3, indicating that

TABLE 2

Short-term germination trend of *Angelica sinensis* seeds treated with XG3 bacterial solutions with different concentrations

|  | 11 d | 12 d | 14 d | 15 d | 17 d | 20 d | Final germination rate |
|---|---|---|---|---|---|---|---|
| Control group | 0.00% | 0.00% | 0.00% | 0.00% | 0.00% | 0.00% | 59.52% |
| XG3-0.05 | 0.00% | 1.35% | 4.05% | 5.48% | 10.00% | 20.00% | 70.00% |
| XG3-0.5 | 0.00% | 8.43% | 16.87% | 37.33% | 59.09% | 65.15% | 83.33% |
| XG3-1 | 0.91% | 7.00% | 9.00% | 17.00% | 29.29% | 39.39% | 71.72% | the XG3 strain has the potential to be developed as a microbial agent for preventing and controlling early bolting of *Angelica sinensis*.

Example 5: Screening Experiment for Composite Protectant

The optimal composite protectant of the XG3 microbial agent was optimized through a single-factor test and a central composite design test method.

(1) In the single-factor test, trehalose (mus, 0.5 mg/mL, 1 mg/mL and 2 mg/mL), sucrose (suc, 2.5 mg/mL, 5 mg/mL and 10 mg/mL), sodium glutamate (msg, 0.5 mg/mL, 1 mg/mL and 2 mg/mL) and glucose (glu, 5 mg/mL, 10 mg/mL and 15 mg/mL) were selected as protectants, three concentrations were separately set, sterile water was taken as a control, the survival rate of the lyophilized *Bacillus velezensis* was taken as an index, and the concentrations of the protectants with a good protective effect were selected. According to the screening results of the single-factor test, the proportion of trehalose, sucrose, sodium glutamate and glucose was optimized by adopting the response surface central composite design, and the optimal formula was determined by taking the survival rate of the lyophilized *Bacillus velezensis* as an index.

Figure 4:
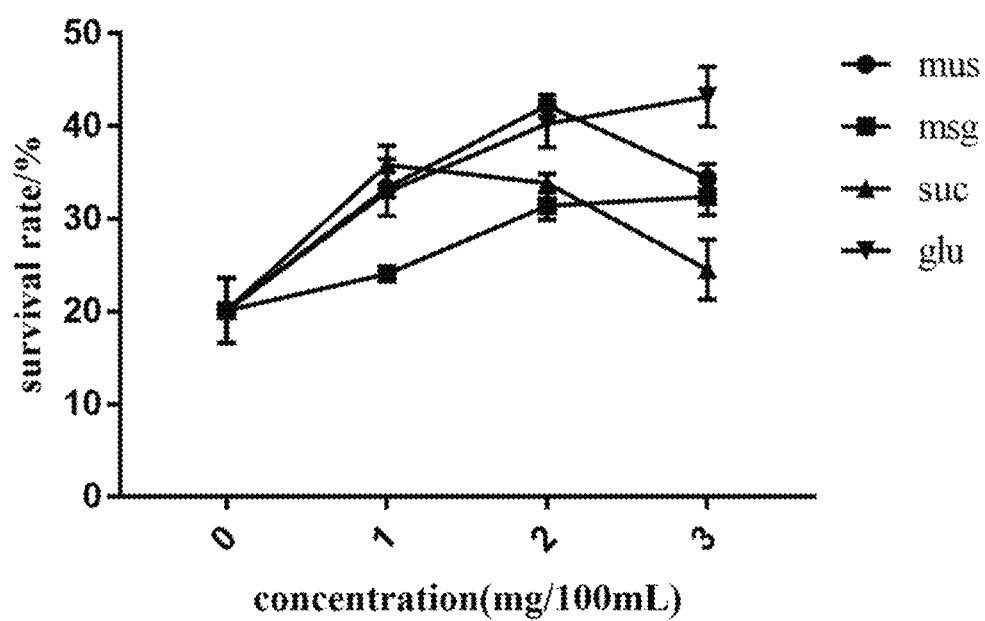
FIG. 4 shows an experiment for screening protectants prepared from a microbial agent of *Bacillus velezensis* XG3.
Figure 5:
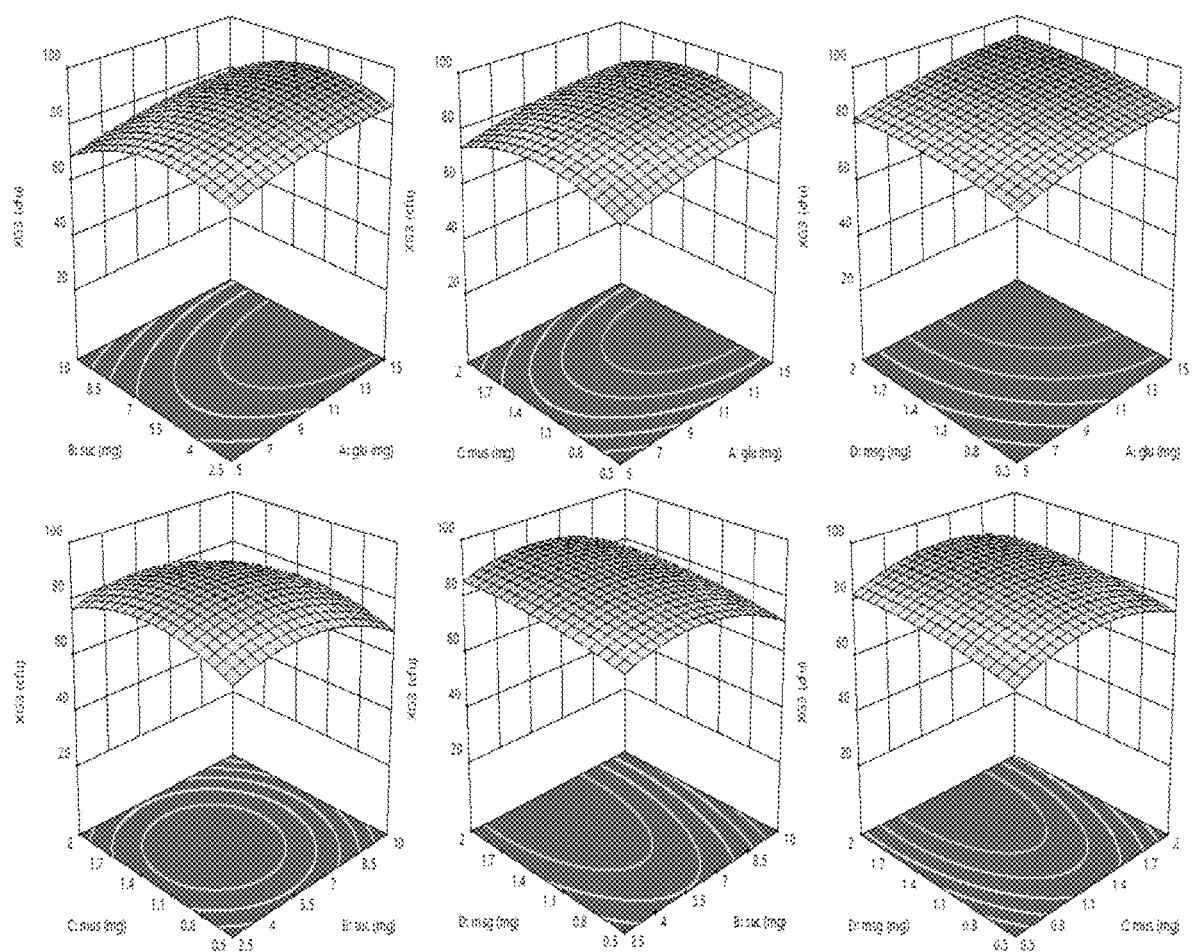
FIG. 5 shows the experimental results of protectants of the microbial agent of *Bacillus velezensis* XG3 by central composite design.
Figure 6:
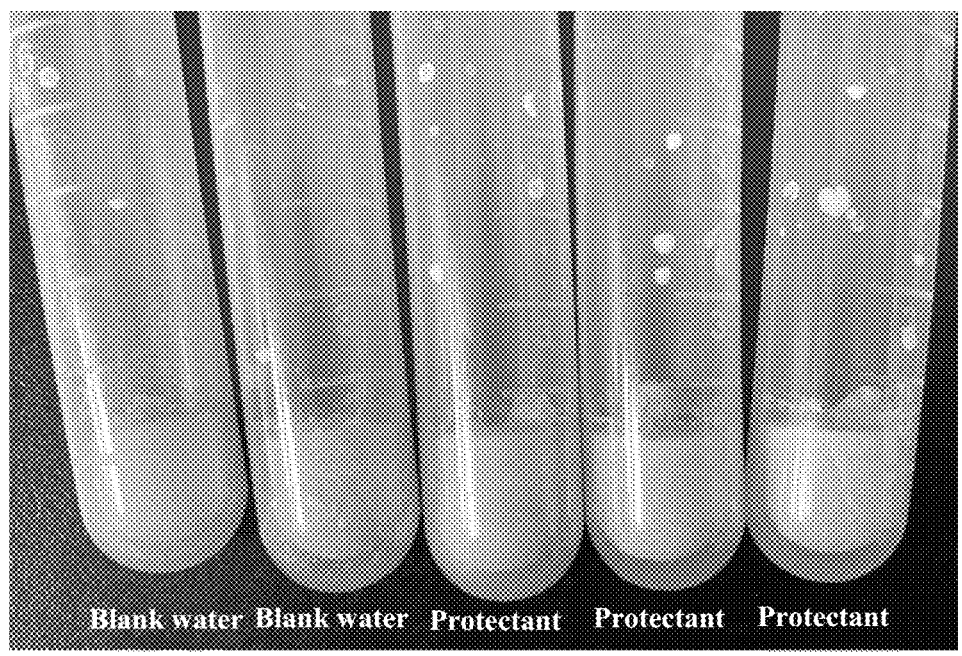
FIG. 6 shows a microbial agent of *Bacillus velezensis* XG3.

(2) In order to increase the number of viable bacteria in the lyophilized powder of the microbial agent, various protectants were usually added before the bacteria were frozen to maintain the activity and stability of the strain. As could be seen from FIG. 4, the survival rate of the lyophilized bacteria was 20.12% when the bacteria were lyophilized with sterile water without the addition of any protectant, and the survival rate of the bacteria increased to various degrees with addition of different protectants. According to the results of the single-factor test, secondary regression fitting was carried out by using Design-Expert 11.0 software to obtain a fitting equation of the survival rate $Y=88.74+5.10A-3.82B+0.2176C+3.22D-2.48A^2-8.17B^2-7.57C^2-1.94D^2$. Analysis of variance (Table 3) showed that the fitted regression equation accorded with the above test principle, the adaptability was good, the optimal formula (FIG. 5) of the XG3 lyophilized protectant obtained by prediction analysis of a regression model was 15 mg/mL glucose, 5.37 mg/mL sucrose, 1.26 mg/mL trehalose and 1.87 mg/mL sodium glutamate, and the predicted survival rate was 87.96%. A verification test was carried out under the formula conditions, the survival rate of XG3 was 82.45%, and the difference between the measured value and the predicted value was small, indicating that the formula was feasible. As could be seen from FIG. 6, the color of the microbial agent powder prepared by lyophilizing the blank water was yellowish, and the color of the microbial agent powder prepared by lyophilizing the protectant was off-white; the volume of the lyophilized protectant was slightly different from that of the protectant before lyophilization, which slightly decreased, and the volume of the lyophilized blank water significantly decreased.

TABLE 3

Analysis of variance of response surface model

| source | sum of squares | df | mean square | F-value | P-value | |
|---|---|---|---|---|---|---|
| Model | 526.79 | 8 | 65.85 | 7.86 | 0.03 | significant |
| A-glu | 57.76 | 1 | 57.76 | 6.89 | 0.06 | |
| B-suc | 37.75 | 1 | 37.75 | 4.51 | 0.10 | |
| C-mus | 0.12 | 1 | 0.12 | 0.01 | 0.91 | |
| D-msg | 26.76 | 1 | 26.76 | 3.19 | 0.15 | |
| AB | 0 | 0 | | | | |
| AC | 0 | 0 | | | | |
| AD | 0 | 0 | | | | |
| BC | 0 | 0 | | | | |
| BD | 0 | 0 | | | | |
| CD | 0 | 0 | | | | |
| $A^2$ | 25.90 | 1 | 25.90 | 3.09 | 0.15 | |
| $B^2$ | 176.34 | 1 | 176.34 | 21.04 | 0.01 | |
| $C^2$ | 151.33 | 1 | 151.33 | 18.06 | 0.01 | |
| $D^2$ | 9.96 | 1 | 9.96 | 1.19 | 0.34 | |
| Residual | 33.52 | 4 | 8.38 | | | |
| Cor Total | 560.31 | 12 | | | | |
| $R^2$ | 0.9402 | | | | | |
| CV % | 8.83 | | | | | |
| Adeq Precision | 9.4299 | | | | | |

Example 6

This example relates to a preparation method for a microbial agent of a *Bacillus velezensis* XG3 strain comprising the following steps:

(1) The *Bacillus velezensis* XG3 strain was inoculated in an LB liquid culture medium and cultured for activation on a thermostatic shaker at 37° C. for 24 h at 140 r/min. The strain activated overnight was transferred at a ratio of 1% (v/v) to a new LB liquid culture medium and cultured at 140 r/min for 24 h. The OD value was measured. The fermentation liquor was centrifuged at 4000 rpm for 5 min, then the supernatant was discarded. The bacterial precipitate was collected.

(2) 1 mL of a composite protectant (15 mg/mL glucose, 5.37 mg/mL sucrose, 1.26 mg/mL trehalose, and 1.87 mg/mL sodium glutamate) solution was added into the bacterial precipitate obtained by centrifugation per 100 mL of the bacterial solution. The sample was pre-frozen in an ultra-low temperature refrigerator at −80° C. After the pre-freezing was completed, the sample was quickly transferred into a vacuum lyophilizer and lyophilized at −40° C. and 10 Pa. Finally, the lyophilized substance was ground, namely lyophilized in vacuum, to obtain a lyophilized XG3 powder microbial agent.

Figure 7:
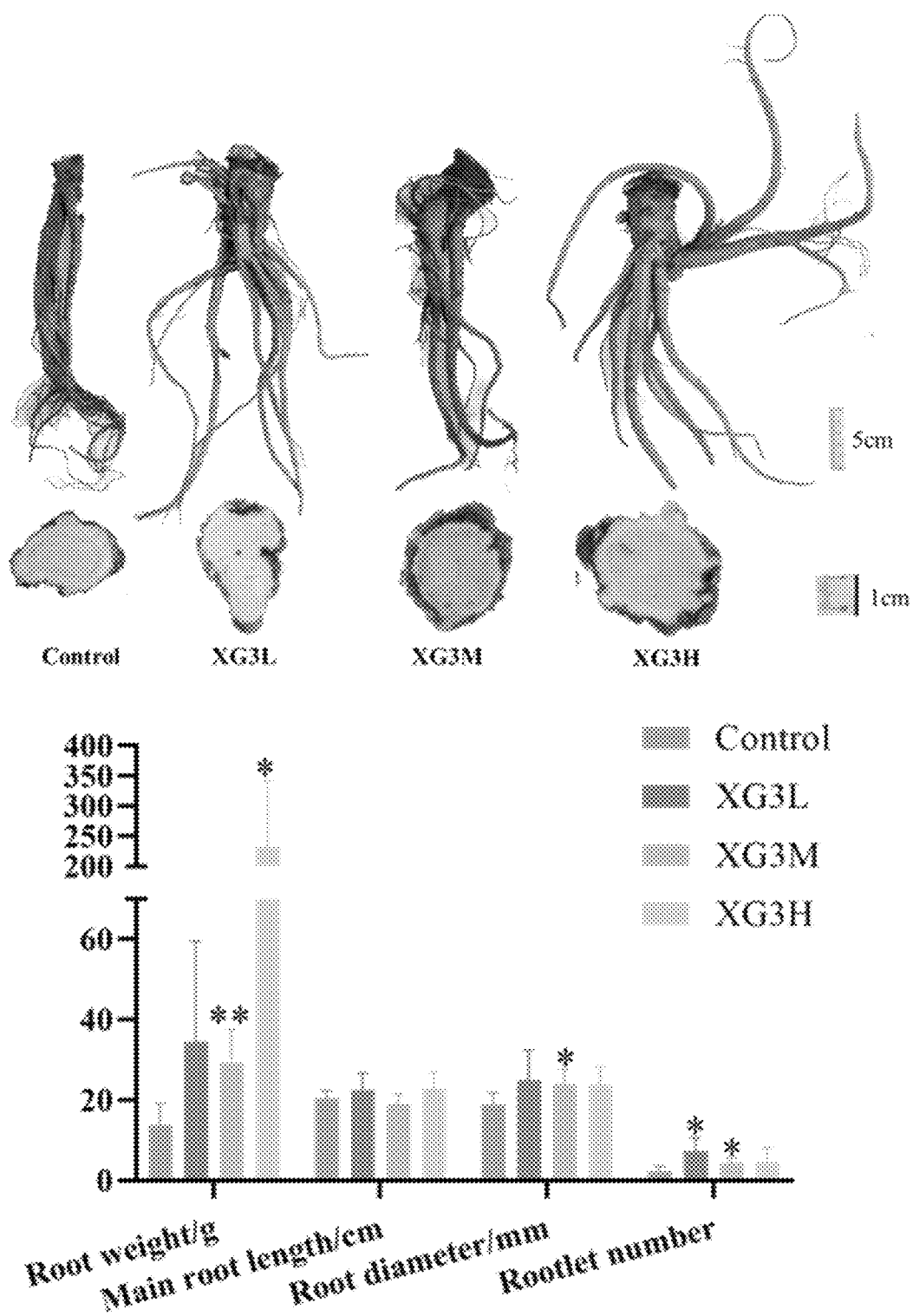
FIG. 7 shows the effect of the microbial agent of *Bacillus velezensis* XG3 on the growth of *Angelica sinensis*.

Example 7. The Effects of the Microbial Agent of *Bacillus velezensis* XG3 on the Growth of *Angelica sinensis* and Early Bolting Prevention and Control were Verified by an Experiment on Test Field Samples The *Angelica sinensis* seedlings not treated by root irrigation were preferred. Blank water was given to the control group at 500 mL per ridge, while the treatment groups received a low-dose at 0.8 g per ridge (XG3L), a medium-dose at 2.4 g per ridge (XG3M), or a high-dose at 7.2 g per ridge (XG3H) of the XG3 microbial agent prepared by the method of Example 6. A total of three interventions were given once every two weeks since one week after the *Angelica sinensis* seedlings turned green. The first intervention was given by root irrigation at 5 mL per plant, and the other two were given by spraying. The effect of the XG3 microbial agent on bolting and flowering and quality formation of *Angelica sinensis* was monitored. The early bolting rate of *Angelica sinensis* in the blank control group was 32.03%, and the early bolting rates of XG3 were 18.75%, 22.27% and 11.72% in the low-dose group, the medium-dose group and the high-dose group, respectively, indicating that the XG3 microbial agent prepared by the present invention could effectively prevent and control the early bolting of *Angelica sinensis*. In addition, as shown in FIG. 7, the microbial agent prepared by the present invention could also significantly increase the yield of *Angelica sinensis*, the diameter of a main root and the number of rootlets.

The above results show that *Bacillus velezensis* XG3, a new *angelica* rhizosphere bacterium, is obtained by screening in the present invention, and the separation, culture, storage and growth promotion function analysis thereof and the preparation method for a microbial agent thereof are established, the *Bacillus velezensis* XG3 has the good functions of promoting seed germination and plant growth of *Angelica sinensis* and delaying the flowering of *Arabidopsis thaliana*, and the microbial agent developed and prepared therefrom can effectively prevent and control early bolting of *Angelica sinensis* and increase the yield of *Angelica sinensis*, and has important practical application values.

The above descriptions are only preferred embodiments of the present invention. It should be noted that those of ordinary skill in the art can also make several improvements and modifications without departing from the principle of the present invention, and such improvements and modifications shall fall within the protection scope of the present invention.

What is claimed is:

1. A method for preventing and controlling early bolting of *Angelica sinensis*, comprising a step of administering *Bacillus velezensis* XG3 on the *Angelica sinensis*, wherein the *Bacillus velezensis* XG3 deposited at China Center for Type Culture Collection (CCTCC) under CCTCC NO: M 2021767.

* * * * *